United States Patent

Ammermann et al.

[11] Patent Number: 5,877,201
[45] Date of Patent: Mar. 2, 1999

[54] FUNGICIDAL MIXTURES

[75] Inventors: Eberhard Ammermann, Heppenheim; Gisela Lorenz, Hambach; Dietrich Mappes, Westheim; Klaus Schelberger, Gönnheim; Manfred Hampel, Neustadt, all of Germany

[73] Assignee: BASF Aktiengesellschaft, Ludwigshafen, Germany

[21] Appl. No.: 750,636

[22] PCT Filed: Jun. 8, 1995

[86] PCT No.: PCT/EP95/02210

§ 371 Date: Dec. 16, 1996

§ 102(e) Date: Dec. 16, 1996

[87] PCT Pub. No.: WO95/35033

PCT Pub. Date: Dec. 28, 1995

[30] Foreign Application Priority Data

Jun. 17, 1994 [DE] Germany ............ 44 21 041.8

[51] Int. Cl.[6] .......... A01N 37/12; A01N 37/44; A01N 43/38

[52] U.S. Cl. .......... 514/417; 514/421; 514/539

[58] Field of Search ............ 514/417, 421, 514/539

[56] References Cited

U.S. PATENT DOCUMENTS

| | | | |
|---|---|---|---|
| Re. 33,989 | 7/1992 | Wenderoth et al. | 514/522 |
| 2,553,770 | 5/1951 | Kittleson | 167/33 |
| 2,553,771 | 5/1951 | Kittleson | 260/313 |
| 2,553,776 | 5/1951 | Kittleson | 260/326 |
| 4,829,085 | 5/1989 | Wenderoth et al. | 514/522 |

FOREIGN PATENT DOCUMENTS

| | | |
|---|---|---|
| 2132698 | 9/1994 | Canada . |
| 254 426 | 1/1988 | European Pat. Off. . |
| 645 088 | 3/1995 | European Pat. Off. . |
| 741 970 | 11/1996 | European Pat. Off. . |
| 2267644 | 12/1993 | United Kingdom . |
| 2279568 | 1/1995 | United Kingdom . |
| 95/15083 | 6/1995 | WIPO . |

OTHER PUBLICATIONS

*Chem. Abst.*, vol. 118, No. 23, Abs. No. 228112.
*Research Disclosure*, No. 338, 1992.

Primary Examiner—Allen J. Robinson
Attorney, Agent, or Firm—Keil & Weinkauf

[57] ABSTRACT

A fungicidal mixture containing
a) the oxime ether carboxylic acid ester of the formula I and
b) a phthalimide derivative selected from the group of compounds II and III

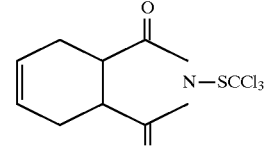

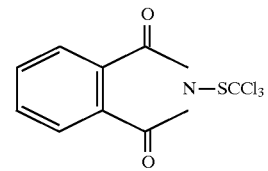

in a synergistically active amount.

12 Claims, No Drawings

FUNGICIDAL MIXTURES

This application is a 371 of PCT/EP95/02210, filed Jun. 8, 1995.

The present invention relates to a fungicidal mixture which contains a) an oxime ether carboxylic acid ester of the formula I

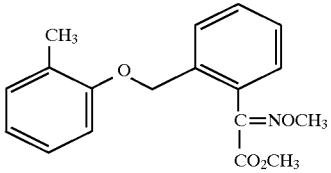

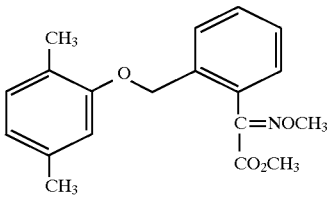

and b) a phthalimide derivative selected from the group of compounds II and III

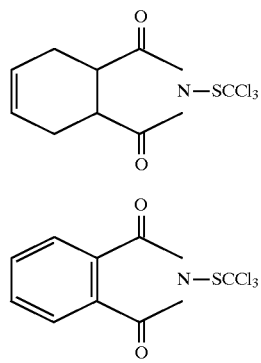

in a synergistically active amount.

The invention additionally relates to methods of controlling harmful fungi using mixtures of the compounds I (i.e., Ia or Ib) and II or of the compounds I and III and the use of the compound I, the compound II and the compound III for the production of mixtures of this type.

The compounds of the formula I, their preparation and their action against harmful fungi are disclosed in the literature (EP-A 253 213).

The phthalimide derivatives II and III (U.S. Pat. Nos. 2,553,770; 2,553,771; 2,553,776), their preparation and their action against harmful fungi are likewise known.

With respect to a decrease in the application rates and an improvement of the spectrum of action of known compounds, the present invention is based on mixtures which, with a reduced total amount of applied active compounds, have an improved action against harmful fungi (synergistic mixtures).

Accordingly, the mixtures defined at the beginning have been found. It has additionally been found that on simultaneous joint or separate application of the compound I and the compound II or the compound III or on application of the compound I and the compound II or the compound III successively harmful fungi can be controlled better than with the individual compounds.

The compounds of the formula I can be present in the E or the Z configuration with respect to the C=X double bond (with respect to the carboxylic acid function group). Accordingly, they can be used in the mixture according to the invention in each case either as the pure E or Z isomer or as an E/Z isomer mixture. The E/Z isomer mixture or the E isomer is preferably used, the E isomer being particularly preferred.

Preferably, the pure active compounds I and II or III are employed in the preparation of the mixtures, to which, if required, further active compounds against harmful fungi or other pests such as insects, arachnids or nematodes, or alternatively herbicidal or growth-regulating active compounds or fertilizers, can be admixed.

The mixtures of the compounds I and II or I and III and the simultaneous joint or separate use of the compounds I and II or I and III are distinguished by an outstanding action against a wide spectrum of phytopathogenic fungi, in particular from the Ascomycetes and Basidiomycetes class. In some cases they are systemically active and can therefore also be employed as foliar and soil fungicides.

They have particular importance for the control of a multiplicity of fungi on various crop plants such as cotton, vegetable plants (eg. cucumbers, beans and cucurbits), barley, grass, oats, coffee, maize, fruit plants, rice, rye, soybean, grape, wheat, decorative plants, sugar cane and a multiplicity of seeds.

In particular, they are suitable for the control of the following phytopathogenic fungi: *Erysiphe graminis* (powdery mildew) on cereals, *Erysiphe cichoracearum* and *Sphaerotheca fuliginea* on cucurbits, *Podosphaera leucotricha* on apples, *Puccinia* species on cereals, *Rhizoctonia* species on cotton and lawns, *Ustilago* species on cereals and sugar cane, *Venturia inaequalis* (scab) on apples, *Helminthosporium* species on cereals, *Septoria nodorum* on wheat, *Botrytis cinerea* (gray mold) on strawberries and vines, *Cercospora arachidicola* on groundnuts, *Pseudocercosporella herpotrichoides* on wheat and barley, *Pyricularia oryzae* on rice, *Phytophthora infestans* on potatoes and tomatoes, *Plasmopara viticola* on vines, *Alternaria* species on vegetables and fruit and also *Fusarium* and *Verticillium* species.

They are additionally applicable in the protection of materials (eg. wood preservation), for example against *Paecilomyces variotii*.

The compounds I and II or I and III can be applied simultaneously jointly or separately, or successively, the sequence in the case of separate application in general having no effect on the control success.

The compounds I and II or I and III are customarily applied in a weight ratio of from 1:1 to 1:1000, preferably from 1:1 to 1:500, in particular from 1:3 to 1:300 (I:II or III).

Depending on the type of effect desired, the application rates of the mixtures according to the invention are from 0.02 to 5 kg/ha, preferably from 0.05 to 3.5 kg/ha, in particular from 0.1 to 3.5 kg/ha. The application rates here for the compound I are from 0.005 to 0.5 kg/ha, preferably from 0.01 to 0.5 kg/ha, in particular from 0.01 to 0.3 kg/ha. The application rates for the compound II or the compound III are correspondingly from 0.1 to 5 kg/ha, preferably from 0.1 to 3.5 kg/ha.

In the treatment of seed, application rates of mixture of from 0.001 to 50 g/kg of seed, preferably from 0.01 to 10 g/kg, in particular from 0.01 to 5 g/kg, are in general used.

If harmful fungi which are pathogenic for plants are to be controlled, the separate or joint application of the compounds I and II or I and III or of the mixtures of the compounds I and II or I and III is carried out by spraying or dusting the seeds, the plants or the soils before or after sowing of the plants or before or after emergence of the plants.

The fungicidal synergistic mixtures and the compounds I and II or I and III according to the invention can be prepared, for example, in the form of directly sprayable solutions, powders and suspensions or in the form of high-percentage aqueous, oily or other suspensions, dispersions, emulsions, oil dispersions, pastes, dusting compositions, broadcasting compositions or granules and applied by spraying, atomizing, dusting, broadcasting or watering. The application form is dependent on the intended use; it should in each case guarantee a dispersion of the mixture according to the invention which is as fine and uniform as possible.

The formulations are prepared in a manner known per se, eg. by addition of solvents and/or carriers. Inert additives such as emulsifiers or dispersants are customarily admixed to the formulations.

Suitable surface-active substances are the alkali metal, alkaline earth metal or ammonium salts of aromatic sulfonic acids, eg. lignosulfonic acid, phenolsulfonic acid, naphthalenesulfonic acid, and dibutylnaphthalenesulfonic acid, as well as of fatty acids, alkyl- and alkylarylsulfonates, alkyl-, lauryl ether and fatty alcohol sulfates, and also salts of sulfated hexa-, hepta- and octadecanols or fatty alcohol glycol ethers, condensation products of sulfonated naphthalene and its derivatives with formaldehyde, condensation products of naphthalene or of naphthalene-sulfonic acids with phenol and formaldehyde, polyoxyethylene octylphenol ethers, ethoxylated isooctyl-, octyl- or nonylphenol, alkylphenol or tributylphenyl polyglycol ethers, alkylaryl polyether alcohols, isotridecyl alcohol, fatty alcoholethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powder, broadcasting and dusting compositions can be prepared by mixing or joint grinding of the compounds I and II or I and III or the mixture of the compounds I and II or I and III with a solid carrier.

Granules (eg. coated, impregnated or homogeneous granules) are customarily prepared by binding the active compound or the active compounds to a solid carrier.

Fillers or solid carriers used are, for example, mineral earths such as silica gel, silicic acids, silicates, talc, kaolin, limestone, lime, chalk, bole, loess, clay, dolomite, diatomaceous earth, calcium and magnesium sulfate, magnesium oxide, ground plastics, and fertilizers such as ammonium sulfate, ammonium phosphate, ammonium nitrate, ureas and vegetable products such as cereal flour, tree bark meal, wood meal and nutshell meal, cellulose powder or other solid carriers.

The formulations in general contain from 0.1 to 95% by weight, preferably from 0.5 to 90% by weight, of one of the compounds I and II or I and III or the mixture of the compounds I and II or I and III. The active compounds are in this case employed in a purity of from 90% to 100%, preferably from 95% to 100% (according to NMR spectrum or HPLC).

The compounds I and II or I and III and the mixtures or the corresponding formulations are applied by treating the harmful fungi or the plants, seeds, soils, surfaces, materials or spaces to be kept free from them with a fungicidally active amount of the mixture, or of the compounds I and II or I and III in the case of separate application. Application can be carried out before or after attack by the harmful fungi.

Examples illustrating the synergistic action of the compounds according to the invention on harmful fungi.

The fungicidal action of the compounds and mixtures thereof is illustrated in the following experiments:

The active ingredients were formulated as 20% strength emulsions in a mixture of 70 wt % of cyclohexanone, 20 wt % of Nekanil® LN (Lutensol® AP6, a spreader-sticker having an emulsifying and dispersing action and based on ethoxylated alkylphenols) and 10 wt % of Emulphor® EL (Emulan® EL, an emulsifier based on ethoxylated fatty alcohols), and diluted to the desired concentration with water.

The leaf area under fungus attack was then assessed in percent. These figures were then converted into degrees of action. The expected degrees of action of the active ingredient composition were determined in accordance with the Colby formula (Colby, S. R., "Calculating synergistic and antagonistic responses of herbicide combinations", Weeds, 15, pp. 20–22, 1967) and compared with the degrees of action observed.

$$\text{Colby formula } E = x + y - \frac{x \cdot y}{100}$$

E=expected degree of action, expressed in % of the untreated control, when active ingredients A and B are used in concentrations of m and n x=degree of action, expressed in % of the untreated control, when active ingredient A is used in a concentration of m y=degree of action, expressed in % of the untreated control, when active ingredient B is used in a concentration of n With a degree of action of 0, the leaf attack of the treated plants corresponds to that of the untreated control plants; a degree of action of 100 means that the treated plants exhibit no leaf attack.

Action on *Botrytis cinera*

Paprika seedlings of the "Neusiedler Ideal Elite" variety having 4 to 5 leaves were sprayed to runoff with the active ingredient formulations. After the sprayed-on layer had dried, the plants were treated with a conidial suspension of the fungus *Botrytis cinera*, and kept for 5 days at 22°–24° C. and high humidity. Leaf attack was then assessed visually.

| Active ingredient | Application rate [ppm] | Degree of action observed | calculated |
|---|---|---|---|
| –/– | –/– | 0 | |
| Ia | 125 | 15 | |
| III | 125 | 80 | |
| Ia + III | 125 + 125 | 95 | 83 |

We claim:

1. A fungicidal mixture containing a) a compound I selected from the group of oxime ether carboxylic acid esters of the formulae Ia and Ib

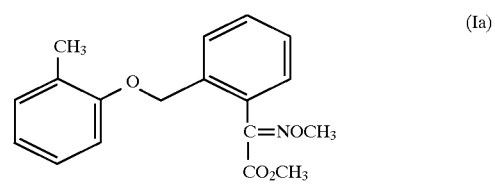

-continued

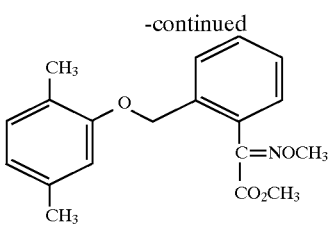
(Ib)

and b) a phthalimide derivative selected from the group of compounds II and III

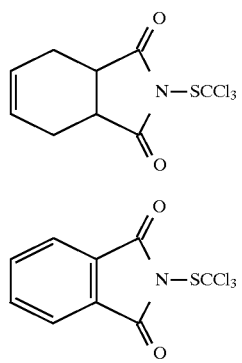
(II)

(III)

in synergistically effective amounts.

2. A fungicidal mixture as claimed in claim 1, containing a compound I as defined in claim 1 and the phthalimide derivative II.

3. A fungicidal mixture as claimed in claim 1, containing a compound I as defined in claim 1 and the phthalimide derivative III.

4. A fungicidal mixture as claimed in claim 1, wherein the weight ratio of the compound I to the compound II or the compound III is from 1:1 to 1:1000.

5. A fungicidal mixture as claimed in claim 1, containing the oxime ether carboxylic acid ester of the formula Ia as defined in claim 1 and the phthalimide derivative II.

6. A fungicidal mixture as claimed in claim 1, containing the oxime ether carboxylic acid ester of the formula Ia as defined in claim 1 and the phthalimide derivative III.

7. A fungicidal mixture as claimed in claim 1, containing the oxime ether carboxylic acid ester of the formula Ib as defined in claim 1 and the phthalimide derivative II.

8. A fungicidal mixture as claimed in claim 1, containing the oxime ether carboxylic acid ester of the formula Ib as defined in claim 1 and the phthalimide derivative III.

9. A method of controlling harmful fungi, which comprises treating the harmful fungi, their environment or the plants, seeds, soils, surfaces, materials or spaces to be kept free from said fungi with a synergistically effective, amount of the compound I as defined in claim 1 and the compound, II as defined in claim 1 or the compound III as defined in claim 1.

10. The method of claim 9, wherein the compound I and the compound II or the compound III are applied simultaneously jointly or separately, or in succession.

11. The method of claim 9, wherein from 0.005 to 0.5 kg/ha of the compound I are applied.

12. The method of claim 9, wherein from 0.1 to 5 kg/ha of the compound II or the compound III are applied.

* * * * *